United States Patent [19]

Eichenbaum

[11] 4,386,927
[45] Jun. 7, 1983

[54] DEVICE TO BE UTILIZED IN EXTRACAPSULAR CATARACT SURGERY

[75] Inventor: Daniel M. Eichenbaum, Chappaqua, N.Y.

[73] Assignee: Ocular Associates, Hollywood, Fla.

[21] Appl. No.: 285,635

[22] Filed: Jul. 21, 1981

Related U.S. Application Data

[63] Continuation of Ser. No. 84,180, Oct. 12, 1979, abandoned.

[51] Int. Cl.³ .............................................. A61M 1/00
[52] U.S. Cl. ...................................................... 604/51
[58] Field of Search ............... 128/276, 297, 240, 241, 128/247; 206/364, 365; 433/81, 84, 82, 91, 100; 604/32, 33, 248, 51

[56] References Cited

U.S. PATENT DOCUMENTS

| Re. 28,405 | 5/1975 | Sollerud | 15/321 |
|---|---|---|---|
| 1,503,579 | 8/1924 | Dewey | 128/241 |
| 3,478,430 | 11/1969 | Park et al. | 433/80 |
| 3,994,297 | 11/1976 | Kopf | 128/276 |
| 4,069,814 | 1/1978 | Clemens | 128/240 |
| 4,091,922 | 5/1978 | Egler | 206/364 |
| 4,157,718 | 6/1979 | Baehr | 128/276 |
| 4,184,491 | 1/1980 | McGannon | 128/276 |
| 4,299,221 | 11/1981 | Phillips et al. | 128/276 |

FOREIGN PATENT DOCUMENTS

| 532271 | 10/1956 | Canada | 433/80 |
|---|---|---|---|
| 2758909 | 9/1978 | Fed. Rep. of Germany | 128/276 |

OTHER PUBLICATIONS

Basic Mechanics of Fluids, Rouse et al., John Wiley and Sons, Inc., New York, N.Y., 1953.
"Opthalmic Microsurgery", *Workshop in Microsurgery*, Singapore, Malaysia, May 9-14, 1977, 604 Library.
"Aspiration Method of a Hard Cataract", Kuwahave, Igaku, Shoin Ltd., Tokyo, Japan, 1972.
Catalog, Welch Scientific Co., Skokie, Ill., "Transparent Plastic Tubing", No. 5513, p. 574, 1965.
Brochure "Cavitron Surgical Systems".

*Primary Examiner*—Richard J. Apley
*Assistant Examiner*—J. L. Kruter
*Attorney, Agent, or Firm*—Richard M. Saccocio

[57] ABSTRACT

Disposable irrigation and aspiration apparatus is disclosed for use during extracapsular extraction of a cataract from a person's eye. A separate handpiece is provided to allow the surgeon to apply only irrigation flow to the eye during the operation. The irrigation-aspiration and irrigation handpieces are connected by a valve to give the operating surgeon his choice of instruments without changing the rate of irrigation flow. The outer surfaces of both handpieces are obstruction free to give the surgeon a high degree of preciseness and maneuverability.

6 Claims, 3 Drawing Figures

DEVICE TO BE UTILIZED IN EXTRACAPSULAR CATARACT SURGERY

This is a continuation, of application Ser. No. 06/084,180, filed Oct. 12, 1979 now abandoned.

BACKGROUND OF THE INVENTION

1. Field of the Invention

This invention relates, in general, to the field of surgical devices for removal of cataracts from a person's eye and, in particular, to apparatus employing aspiration and irrigation for extracapsular extraction of an opaque lens, with or without a nucleus, or cataract from an eye of a patient.

2. Description of the Prior Art

It is well known that cataracts are caused by opacification of the lens of the eye. At about age 20, a person's lens forms a nucleus which becomes larger and harder with age. The material surrounding the nucleus of a cataractous lens is known as the cortex. Depending upon its severity, cataracts cause poor vision or even an almost complete inability to see. While old age is probably the primary cause of cataracts, there are other causes. Thus, cataracts have been known to exist in every age group and in every race. There are records verifying knowledge of the existence of cataracts dating back for many centuries.

There is only one type of treatment for cataracts: surgery. There are no drugs or other treatment which will make cataracts dissolve or disappear. Usually age and the amount and degree of opaqueness is determinative of whether or not surgery is warranted. In children, the lens is soft and flexible and a clear lens is able to change its power accommodation. In older persons, the lens is less resilient and cannot very well adjust near focus. In the latter case, glasses can correct the deficiency. However, as previously stated, surgery is the only treatment for cataracts whether the patient is young or old.

Since cataracts only affect the lens of an eye, removal of the lens and its replacement by either glasses, contact lenses, or the newly devised technique of lens implantation can and does restore a person's sight. Many techniques, each with its own disadvantages and advantages for removal of the lens, have been developed over the ages. Understandably, the early techniques were not very successful, while modern day techniques are highly successful. Cataract surgery originated in India, Greece and Arabia. The first known procedure of cataract surgery, which dates back to the first century, is alternatively termed as couching, depression, or reclination. In that technique, the opaque lens is displaced into the vitreous humor of the eyeball. This early operative technique caused various complications that often led to blindness. Development of the couching technique, by different operating methods and equipment, tended to lessen the effect and after effects of the surgery, but could not and did not eliminate its basic deficiencies or limitations. As a result, totally different surgical methods were needed and were developed.

A technique, known today as the aspiration method, was probably first used shortly after the inception of the couching technique. However, the first written description of the aspiration method did not appear until the eleventh century. An Arabian ophthalmologist by the name of Ammar ibn Ali is generally credited as being the inventor of the method of aspiration because, in part, of his approach which avoided a failure known as humor loss. By entering the eye through the sclera instead of the cornea, Ammar ibn Ali was able to prevent loss of aqueous humor which would have resulted by entering the eye through the cornea.

In 1745, Jacques Daviel of France, made an incision in the lower margin of the eye, cut through the lens capsule, and extracted the cataract. His innovation overcame many of the complications caused by the couching technique and was considered highly successful. Modern variations of the innovations of Daviel and Ali have resulted in today's routine methods of cataract removal which are virtually one-hundred percent successful.

Regardless of whether a cataract is removed by aspiration, or actually delivering the cataract from the eye, or by a combination of these methods, surgical removal of cataracts in today's technology is broadly classified as intracapsular or extracapsular removal. With intracapsular removal, the lens and its outer covering, the lens capsule, are both removed. With extracapsular removal, the anterior portion of the lens capsule is cut away from the lens and the cataract is then removed. Intracapsular extraction of cataracts is the most prevalent technique employed by today's ophthalmologists.

A relatively good history of the techniques employed to remove cataracts may be found in, "Aspiration Method of a Hard Cataract," by Yasuharu Kuwahare, M.D., Igaku Shoin Ltd., Tokyo, 1972. Another reference is, "Phacoemulsification and Aspiration," "The Kelman Technique of Cataract Removal," by Charles D. Kelman, M.D. Aesulapius Publishing Co., Ala., 1975. These references also contain information concerning the equipment or apparatus utilized to aspirate both hard and soft cataracts from an eye. In referring to these references, however, it is to be realized that the subject matter of this patent application applies only to aspiration and irrigation apparatus which aspirates either soft cataracts or the cortex of hard cataracts by th extracapsular technique.

Typically, modern aspiration and irrigation apparatus includes a handpiece, held by the operating surgeon, having suction and irrigation lines connected thereto and a needle eminating therefrom. The suction line is usually connected to a vacuum pump. In the past, a syringe or the surgeon's mouth was used to create the vacuum which sucked the lens from the eye. The irrigation line is connected to a reservoir of appropriate liquid which is pumped to the anterior chamber of the eye to maintain its form during the surgery. The needle, having both suction and irrigation capabilities is inserted through an incision in the eye and is placed in physical contact with the lens to effectuate aspiration.

The irrigation-aspiration apparatus of the prior art is made to be reused for an unlimited number of operations; hence, it is required that it be capable of being sterilized. The reuseable requirement also results in the requirement that the vacuum and fluid connections be resealable time after time after disassembly or after needle or handpiece changes. It also requires exact fits between the interchangeable components.

Because of the hard service experienced by the prior art apparatus, it had to be designed to be very strong; hence, it is usually heavy and relatively unwieldly. Metal tubing or other devices connected to the outer surface of the handpiece also contribute to inadequate handling characteristics. Needless to say, cataract surgery is a very delicate operation and proper maneuverability of the aspiration and irrigation needle is an essential requirement. Naturally, therefore, proper gripping characteristics of the handpiece and lack of external obstructions on the handpiece are prerequisites to proper placement of the needle within the eye and its subsequent manipulation. The apparatus of the prior art suffers from a lack of adequate handling characteristics.

In that the devices of the prior art are reuseable, it is not uncommon for dried and hard pieces of aspirated portions of the eye to be lodged within the instrument or its tubing. Such a situation causes inconsistent vacuum levels, or unknown vacuum levels at the tip of the aspiration needle, or even worse, actual blockage of the vacuum. This leads to inconsistencies from one operation to another. Indeed, over a prolonged number of operations, the device may fail to function entirely and such failure may occur at a most inopportune time.

Another problem associated with the devices of the prior art involve kinking of the permanent tubing attached to the devices. This may occur from dropping the device during its long lifetime or from abuse during cleaning, assembly or disassembly of the unit. Of course, straightening of the kink will somewhat correct this condition, but permanent damage may have occured such as a fracture of the metal. Consider such possibilities and the effects of the same in view of the distinct probability that the operating surgeon is not aware of the defective condition.

Accordingly, it is an object of the present invention to provide irrigation-aspiration apparatus for use with extracapsular extraction of cataracts which requires no operating room sterilization and is disposable after one operation.

Another object of the present invention is to provide a surgical device which does not require assembly prior to use by the operating surgeon.

A further object of the invention is to provide cataract surgical apparatus which assures leak-free and vacuum-tight joint connections.

A still further object of the present invention is to provide apparatus for cataract surgery which is virtually kinkless.

An even further object of the invention is to provide a disposable device which assures consistency of vacuum flow and irrigation flow from one device to another.

Still an even further object of the present invention is to provide apparatus which is lightweight and easily maneuvered by the operating surgeon to allow precise location and movement of the aspiration and irrigation tips within the eye.

Another object of the present invention is to provide a device which does not necessitate disconnecting and reconnecting different handpieces to obtain irrigation without aspiration.

BRIEF SUMMARY OF THE INVENTION

In accordance with the above objectives, the present invention comprises improved irrigation-aspiration apparatus for extracapsular removal of a cataract. The apparatus which is preassembled and sterilized includes an essentially cylindrical irrigation and aspiration handpiece, an essentially cylindrical irrigation handpiece, connecting plastic tubing, appropriate valving and an irrigation-aspiration needle. All connections to either handpiece are made internal to the handpiece to assure an obstruction-free outer diameter which in turn insures precise maneuverability of the handpiece by the surgeon. The handpieces are made from a lightweight material to eliminate fatigue of the hands and arms of the operating surgeon to enhance "feel" of the instrument and improve operational success.

BRIEF DESCRIPTION OF THE DRAWINGS

For a more complete understanding of the invention, reference is had to the following description taken in conjunction with the accompanying drawings, in which.

DESCRIPTION OF THE PREFERRED EMBODIMENTS

Figure 1:
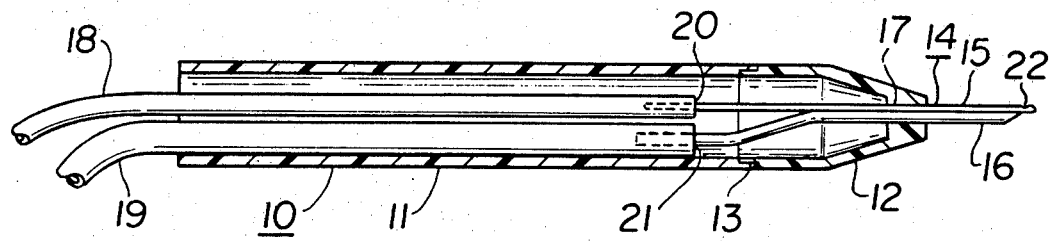
FIG. 1 is a cross-sectional view of the inventive irrigation-aspiration handpiece illustrating the irrigation flow channel and the aspiration flow channel from the irrigation-aspiration needle through the handpiece.

Referring now to FIG. 1 of the drawings, the improved handpiece of the inventive apparatus is shown therein and generally designated by the numeral 10. Handpiece 10 comprises a body 11 and a tip portion 12. Tip portion 12 and body 11 are made from a dimensionally stable plastic which is capable of being both extruded and die cast. In this manner, handpiece 10 may be assembled from an extruded body 11 and a cast tip portion 12 which are press fitted together at their respective ends 13. Body 11 has an overall length of approximately 5 to 6 inches and has an outer diameter of approximately five-eights to three-quarters of an inch. The wall thickness of body 11 is within the range of one-sixteenth to one-eighth of an inch. Tip portion 12 is approximately one inch in length. While the above-stated dimensions have been found to have a satisfactory "feel" from an operating surgeon's viewpoint, reasonable variations in the dimensions would also result in a satisfactory handpiece and are intended to be included within the scope of this application.

In the embodiment shown, needle 14 is an over and under or double barreled cannula for purposes of both irrigation and aspiration. This type of needle and its variations are well known in the art. Tip portion 12 includes an essentially circular opening 17 for a press fit accommodation of needle 14. That is, needle 14 is frictionally held in place in tip portion 12 based on the size of opening 17 and the combined maximum cross-sectional dimension of aspiration needle 15 and irrigation needle 16.

Tip portion 12 is tapered and outwardly extends from body 11 with opening 17 in the outermost end of tip portion 12 and with needle 14 fitting in opening 17. Care must be taken to insure that the press fit of needle 14 in tip portion 12 is sufficiently substantial such that there is absolutely no motion between the two components during the cataract extraction operation.

Plastic tubing, which is preferably transparent, is attached to needles 15 and 16 within body 11. Although tubing 18 is shown and is smaller than tubing 19, the effulent or aspiration flow is substantially equal to the influent or the irrigation flow. These flows are balanced by equipment attached to tubes 18 and 19, but not shown. Transparent tubing aids in the discovery of particle accumulation or the presence of air bubbles in the lines which can operate to block the flow in lines 18 and 19. Obviously, such flow blockage is very objectionable; on the other hand, locating the cause of the blockage and the ability to clear the lines could avoid a catastrophy.

Tubing 18 and 19 are highly elastic and are provided with fairly thick walls in relation to their inside diameter. Tubing 19, for example, may have an inside diameter of approximately one-eighth of an inch and an outside diameter of approximately one-quarter of an inch. Tubing 18, which is used for aspiration flow, may have an outside diameter of three-sixteenths of an inch and an inside diameter of one-sixteenth of an inch. The size of tubing 18 must be such that it is relatively insensitive to collapsing under the operational vacuum pressure. Tubing 18 and 19 must also be relatively immune to kinking so that an inadvertent sharp bend during an operation does not cause a kink resulting in interruption of the flow. Tubing with high elasticity or resiliency is required so that little or no effect is required to allow the tubing to assume promptly its original shape upon removal of the kink-causing phenomenon and thereby allow instantaneous resumption of the irrigation and aspiration flow. One further highly desirable characteristic of tubing 18 and 19, is that it not be cohesive to itself. That is, that if the tubing is pinched or kinked, that the inner diameter does not stick to itself and cause a flow blockage. On the other hand, tubing 18 or 19 should not be so rigid that it prevents free and unrestricted maneuverability of the handpiece. In other words, the tail should not wag the dog.

The connections of tubing 18 and 19, with needle 14, are made within handpiece 10. Since it is not possible for an operating surgeon to view the internal workings of handpiece 10, the connections 20 and 21 should be made so that there is no possibility of flow interruption within handpiece 10. This is simply and effectively accomplished by having the inside diameters of tubing 18 and 19 mate with or fit over the outside diameter of needles 14 and 16, respectively.

Since all connections to needle 14 are made internal to handpiece 10, it is to be noted that handpiece 10 has a substantially cylindrical outside diameter. There are no external obstructions. An operating surgeon is thus presented with an instrument which he is capable of precisely rotating and axially positioning in order to locate the aspiration orifice 22 of needle 15 at the exact portion of the lens which he intends to aspirate.

Figure 2:
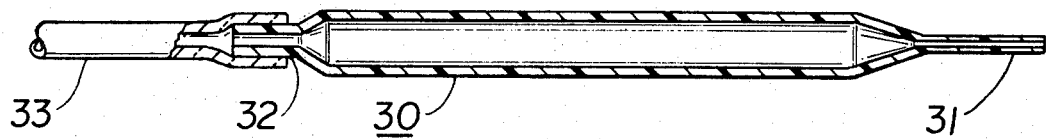
FIG. 2 is a cross-sectional view of the inventive irrigation handpiece illustrating the flow connections thereof; and, FIG. 3 is a schematic drawing of the overall system illustrating the connection between the handpieces of FIG. 1 and FIG. 2.

FIG. 2 depicts an irrigation handpiece generally designated by the numeral 30. It is to be noted that handpiece 30 does not necessarily contain a needle per se. End 31 serves this function. End 31 is integrally formed with handpiece 30. Handpiece 30 may be made by conventional molding processes utilizing a dimensionally stable plastic similar to that of handpiece 10. Of course, a separate needle, either plastic or metal may be utilized in place of the integrally formed needle.

End 31 is sufficiently small so as to approximate the overall size of needle 16. In the embodiment shown, end 32 of handpiece 30 is sized to allow tubing 33 which is the same size as tubing 19, to be connected thereto. As with handpiece 10, handpiece 30 is substantially cylindrical with no external obstructions. Thus, handpiece 30 possesses the same good maneuverability and locatability as does handpiece 10. Handpiece 30 has an overall length of approximately 5 to 6 inches with an outer diameter of approximately three-eighths to one-half of an inch.

Figure 3:
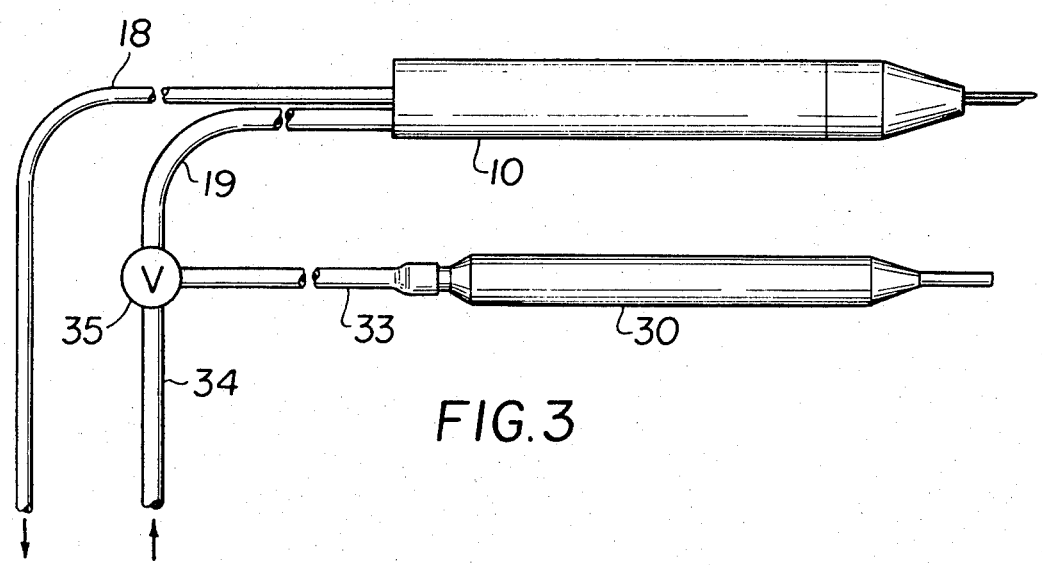

The overall irrigation-aspiration system is shown in FIG. 3. The irrigation lines, lines 19 and 33 of handpieces 10 and 30, respectively, are connected by a valve 35. Valve 35 permits flow through either tubing 33 and handpiece 20 or through tubing 19 and handpiece 10; but, not through both at the same time. Line 34, consisting of tubing the same as that of lines 35 and 19, is also connected to valve 35. Line 34 is also connected to a fluid reservoir having a pump connected thereto. The fluid reservoir and the pump are not shown in the drawings and do not form a part of this invention. The combination of a separate irrigation device and a irrigation-aspiration device which is made operable by simply turning a valve gives a surgeon a degree of flexibility, during an actual operation that the prior art apparatus did not allow. Previously, one handpiece had to be disconnected from the flow source and replaced by another handpiece. This is a relatively timeconsuming procedure and is usually required at a point of time when time is of the essence. The present system of separate but already connected handpieces has another most important advantage. The advantage is that exactly the same rate and volume of irrigation flow is obtained from either handpiece. Changing the direction of flow by turning valve 35, produces exactly the same volume flow rate in either line 19 or 33. With the present invention, there is no need to shut off the irrigation flow, change the handpieces, and then reactivate and readjust the irrigation flow. Since the same flow rate is achieved by turning valve 35, the form of the anterior chamber of the eye is exactly maintained with either handpiece. And, as previously explained, a properly formed anterior chamber throughout the cataract operation is a prerequisite to a successful result.

In use, the apparatus described herein is connected to an appropriate vacuum source and a fluid flow pump. The separate connections in a single entry instrument, handpiece 10, allows for continual monitoring of aspiration and continuous control of anterior chamber depth with balanced inflow and outflow. The instrumentation hook up and adjustment is made prior to its actual use so that it is ready when needed. In the meantime, the patient is in the operating room and all else is ready for the cataract extraction surgery.

The surgeon begins by making an incision in the limbus of the eye of a size of approximately two millimeters using a razor blade knife or other appropriate instrument. A cystotome or a bent disposable 25 gauge, five-eighths of an inch needle is inserted through the two millimeter incision and the anterior of the capsule surrounding the cataractous lens is opened. The nucleus of the lens, if any, is then prolapsed or slid into the anterior chamber of the eye. The incision is enlarged to approximately eight millimeters and the nucleus is delivered or removed from the eye by gently using counterpressure from above. The incision is then reduced in size back to approximately three millimeters.

The latter step, above described, is in preparation of using the present inventive apparatus. The double cannula needle is inserted through the three millimeter incision, past the previous location of the anterior capsule, into the cortex. The cortex being the soft pulpy portion of the lens surrounding the hard nucleus. The cortex is then completely aspirated by the aspiration channel 15 of needle 14. During this phase of the operation, the form of the anterior chamber is maintained by the irrigation flow through channel 16. If at any time during the operation just irrigation flow is required, the surgeon turns valve 35 and utilizes handpiece 30 in place of handpiece 10. The eye is then ready for lens implantation and/or final closure. The irrigation-aspiration apparatus is then discarded in its entirety.

From the foregoing, it is apparent that applicant has provided improved irrigation-aspiration apparatus for use with extracapsular extraction of cataracts.

In the drawings and specification, there has been set forth a preferred embodiment of the invention and although specific items are employed, they are used in a generic and descriptive sense only and not for purposes of limitation. And, while other modifications and changes of the invention may be readily apparent to one skilled in the art, such modifications and changes are intended to be included within the scope of the invention.

I claim:

1. Improved irrigation-aspiration apparatus for use during extracapsular cataract extraction comprising a first elongated hollow housing having a substantially circular cross-sectional shape, having no obstructions thereon, open at one end and closed at its other end, a double barreled cannula needle having a first channel for aspiration and a second channel for irrigation, said needle being mounted within said closed end of said housing with one end of said needle extending within said housing and the other end of said needle extending out from said housing, a first tube attached within said housing to said aspiration channel of said needle, a second tube attached within said housing to said irrigation channel of said needle; and, a second elongated housing having a substantially circular cross-sectional shape, a single channel needle for irrigation attached to one end thereof and extending therefrom, tubing attached to the other end of said housing in flow communication with the channel of said needle, a valve having two outlet ports and one inlet port, said irrigation tubing of said first housing being connected to one of said outlet ports of said valve, said tubing of said housing being connected to the other outlet port of said valve and the inlet port of said valve adapted to be connected to a fluid flow pump.

2. The apparatus of claim 1, wherein said housings, said needles, said valve, and said tubing are preassembled and sterilized.

3. The apparatus of claim 1, wherein said single channel needle is integrally formed with said second housing and extends therefrom.

4. Improved irrigation-aspiration apparatus for use during extracapsular cataract extraction comprising a first elongated hollow housing having a substantially circular cross-sectional shape having no obstructions thereon, open at one end and closed at its other end, a double cannular flow needle having a first channel for aspiration and a second channel for irrigation, said needle being mounted within said closed end of said first housing and with one end of said needle extending within said housing and the other end of said needle extending out from said housing, a first tube attached within said first housing to said aspiration channel of said needle, a second tube attached within said first housing to said irrigation channel of said needle; and, a second elongated housing having a substantially circular cross-sectional shape, a single channel irrigation flow needle attached to one end of said second housing and extending therefrom, tubing attached to the other end of said housing in flow communication with the channel of said needle, a valve having two outlet ports and one inlet port, said irrigation tubing of said first housing being connected to one of said outlet ports of said valve, said tubing of said second housing being connected to the other outlet port of said valve and the inlet port of said valve adapted to be connected to a fluid flow pump.

5. The apparatus of claim 4, wherein said single channel needle is integrally formed with said second housing.

6. The apparatus of claim 4, wherein said housings, said needles, said valve, and said tubing are preassembled and sterilized.